(12) United States Patent
McCombie et al.

(10) Patent No.: US 11,647,910 B2
(45) Date of Patent: May 16, 2023

(54) BODY-WORN SYSTEM FOR CONTINUOUS, NONINVASIVE MEASUREMENT OF VITAL SIGNS

(71) Applicant: SOTERA WIRELESS, INC., Carlsbad, CA (US)

(72) Inventors: Devin McCombie, San Diego, CA (US); Guanqun Zhang, San Diego, CA (US); Isaac Henry, La Mesa, CA (US)

(73) Assignee: SOTERA WIRELESS, INC., Carlsbad, CA (US)

( * ) Notice: Subject to any disclaimer, the term of this patent is extended or adjusted under 35 U.S.C. 154(b) by 249 days.

(21) Appl. No.: 17/114,257

(22) Filed: Dec. 7, 2020

(65) Prior Publication Data

US 2021/0177281 A1    Jun. 17, 2021

Related U.S. Application Data

(63) Continuation of application No. 15/117,162, filed as application No. PCT/US2015/014915 on Feb. 6, 2015, now Pat. No. 10,856,742.

(Continued)

(51) Int. Cl.
*A61B 5/02* (2006.01)
*A61B 5/00* (2006.01)
(Continued)

(52) U.S. Cl.
CPC ........ *A61B 5/02028* (2013.01); *A61B 5/0024* (2013.01); *A61B 5/0261* (2013.01);
(Continued)

(58) Field of Classification Search
CPC . A61B 5/02028; A61B 5/0456; A61B 5/0452; A61B 5/0205
See application file for complete search history.

(56) References Cited

U.S. PATENT DOCUMENTS

| | | | |
|---|---|---|---|
| 5,316,008 | A | 5/1994 | Suga et al. |
| 5,649,543 | A | 7/1997 | Hosaka et al. |

(Continued)

FOREIGN PATENT DOCUMENTS

| | | |
|---|---|---|
| CN | 106028918 A | 10/2016 |
| EP | 3102097 A1 | 12/2016 |

(Continued)

OTHER PUBLICATIONS

Akram et al., A State Optimization Model Based on Kalman Filtering and Robust Estimation Theory for Fusion of Multi-Source Information in Highly Non-linear Systems. Sensors (Basel). Apr. 9, 2019;19(7):1687 (22 pages).

(Continued)

*Primary Examiner* — Michael J D'Abreu
(74) *Attorney, Agent, or Firm* — Acuity Law Group, PC; Michael A. Whittaker

(57) ABSTRACT

The invention provides methods and systems for continuous noninvasive measurement of vital signs such as blood pressure (cNIBP) based on pulse arrival time (PAT). The invention uses a body-worn monitor that recursively determines an estimated PEP for use in correcting PAT measurements by detecting low frequency vibrations created during a cardiac cycle, and a state estimator algorithm to identify signals indicative of aortic valve opening in those measured vibrations.

8 Claims, 4 Drawing Sheets

Related U.S. Application Data

(60) Provisional application No. 61/936,850, filed on Feb. 6, 2014.

(51) Int. Cl.
| *A61B 5/021* | (2006.01) |
| *A61B 5/11* | (2006.01) |
| *A61B 5/316* | (2021.01) |
| *A61B 5/352* | (2021.01) |
| *A61B 5/026* | (2006.01) |
| *A61B 5/0295* | (2006.01) |
| *A61B 5/024* | (2006.01) |

(52) U.S. Cl.
CPC ........ *A61B 5/0295* (2013.01); *A61B 5/02125* (2013.01); *A61B 5/1102* (2013.01); *A61B 5/316* (2021.01); *A61B 5/352* (2021.01); *A61B 5/6826* (2013.01); *A61B 5/7221* (2013.01); *A61B 5/02416* (2013.01); *A61B 5/725* (2013.01); *A61B 5/7253* (2013.01)

(56) References Cited

U.S. PATENT DOCUMENTS

| 5,857,975 | A | 1/1999 | Golub |
| 5,865,755 | A | 2/1999 | Golub |
| 7,569,020 | B2 | 8/2009 | Noren et al. |
| 7,715,909 | B2 | 5/2010 | Zanetti et al. |
| 8,251,911 | B2 | 8/2012 | Macquarrie et al. |
| 8,419,649 | B2 | 4/2013 | Banet |
| 8,430,817 | B1 | 4/2013 | Al-Ali et al. |
| 9,596,999 | B2 | 3/2017 | Moon et al. |
| 10,856,742 | B2 | 12/2020 | McCombie et al. |
| 10,973,414 | B2 | 4/2021 | Moon et al. |
| 2009/0270748 | A1 | 10/2009 | Corbucci et al. |
| 2010/0298650 | A1 | 11/2010 | Moon et al. |
| 2010/0324385 | A1 | 12/2010 | Moon et al. |
| 2011/0208016 | A1 | 8/2011 | Bombardini |
| 2015/0038856 | A1 | 2/2015 | Houlton et al. |

FOREIGN PATENT DOCUMENTS

| WO | 2012149652 A1 | 11/2012 |
| WO | 2013160537 A1 | 10/2013 |
| WO | 2015120330 A1 | 8/2015 |

OTHER PUBLICATIONS

Castiglioni et al., Wearable Seismocardiography. Conf Proc IEEE Eng Med Biol Soc. 2007;2007:3954-3957.

Elson and Romer. Wireless Sensor Networks: A New Regime for Time Synchronization. In Proc. First Workshop or Hot Topics in Networks (HotNets-I), Princeton, NJ, Oct. 28-29, 2002:6 pages.

Elson et al., Fine-Grained Network Time Syncrhonization using Reference Broadcasts. In Proc. 5th Symp. Op. Syst. Design Implementation (OSDI), Boston, MA, Dec. 9-11, 2002:18 pages.

Extended European Search Report issued in EP 15745843 dated Sep. 5, 2017.

First Office Action issued by SIPO in PRC Patent Application No. 2015800107868 dated Nov. 5, 2018—incl Engl lang transl (46 pages total).

International Search Report and Written Opinion issued in PCT/US2015/014915 dated May 14, 2015 (11 pages).

BODY-WORN SYSTEM FOR CONTINUOUS, NONINVASIVE MEASUREMENT OF VITAL SIGNS

The present invention is a continuation of U.S. patent application Ser. No. 15/117,162, filed on Aug. 5, 2016, now U.S. Pat. No. 10,856,742, which was filed under 35 U.S.C. § 371 as the U.S. national phase of International Application No. PCT/US2015/014915, filed on Feb. 6, 2015, which designated the U.S. and claims priority to U.S. Provisional Application No. 61/936,850, filed on Feb. 6, 2014, each of which is hereby incorporated in its entirety including all tables, figures, and claims.

BACKGROUND OF THE INVENTION

The following discussion of the background of the invention is merely provided to aid the reader in understanding the invention and is not admitted to describe or constitute prior art to the present invention.

Pulse oximeters are medical devices featuring an optical module, typically worn on a patient's finger or ear lobe, and a processing module that analyzes data generated by the optical module. The optical module typically includes first and second light sources (e.g., light-emitting diodes, or LEDs) that transmit optical radiation at, respectively, red ($\lambda$~600-700 nm) and infrared ($\lambda$~800-1200 nm) wavelengths. The optical module also features a photodetector that detects transmitted radiation that passes through an underlying artery within, e.g., the patient's finger or earlobe. Typically the red and infrared LEDs sequentially emit radiation that is partially absorbed by blood flowing in the artery. The photodetector is synchronized with the LEDs to detect the transmitted radiation. In response, the photodetector generates a separate radiation-induced signal corresponding to each wavelength. The signal, called a plethysmograph, varies in a time-dependent manner as each heartbeat varies the volume of arterial blood and hence the amount of radiation absorbed along the path of light between the LEDs and the photodetector. A microprocessor in the pulse oximeter digitizes and processes plethysmographs generated by the red and infrared radiation to determine the degree of oxygen saturation in the patient's blood using algorithms known in the art. A number between 94%-100% is considered normal, while a number below 85% typically indicates the patient requires hospitalization. In addition, the microprocessor analyzes time-dependent features in the plethysmograph to determine the patient's heart rate.

Another medical device called an electrocardiograph features conductive electrodes, placed at various locations on a patient's body, that measure electrical signals which pass into an amplification circuit. The circuit generates a waveform called an electrocardiogram, or ECG, that describes a time-dependent response of the patient's cardiovascular system.

Various methods have been disclosed for using both plethysmographs and ECGs, taken alone or in combination, to measure blood pressure. Pulse wave velocity defined as the velocity of a pressure pulse launched by a heartbeat in a patient's arterial system, has been shown in a number of studies to correlate to both systolic (SYS), diastolic (DIA), and mean blood pressures. In these studies, a surrogate for pulse wave velocity known as pulse arrival time (PAT) is typically measured with a conventional vital signs monitor that includes separate modules to determine both an electrocardiogram (ECG waveform) and a value for pulse oximetry (SpO2). During a PAT measurement, multiple electrodes typically attach to a patient's chest to determine a time-dependent component of the ECG waveform characterized by a sharp spike called the 'QRS complex'. The QRS complex indicates an initial depolarization of ventricles within the heart and, informally, marks the beginning of the heartbeat and a pressure pulse that follows. SpO2 is typically measured with a bandage or clothespin-shaped sensor that attaches to a patient's finger, and includes optical systems operating in both red and infrared spectral regions. A photodetector measures radiation emitted from the optical systems that transmits through the patient's finger. Other body sites, e.g., the ear, forehead, and nose, can also be used in place of the finger. During a measurement, a microprocessor analyses both red and infrared radiation measured by the photodetector to determine time-dependent waveforms corresponding to the different wavelengths called photoplethysmographs (PPG waveforms). From these a SpO2 value is calculated. Time-dependent features of the PPG waveform indicate both pulse rate and a volumetric absorbance change in an underlying artery (e.g., in the finger) caused by the propagating pressure pulse.

Typical PAT measurements determine the time separating a maximum point on the QRS complex (indicating the peak of ventricular depolarization) and a portion of the PPG waveform (indicating the arrival of the pressure pulse). PAT depends primarily on arterial compliance, the propagation distance of the pressure pulse (which is closely approximated by the patient's arm length), and blood pressure. To account for patient-specific properties, such as arterial compliance, PAT-based measurements of blood pressure are typically 'calibrated' using a conventional blood pressure cuff. Typically during the calibration process the blood pressure cuff is applied to the patient, used to make one or more blood pressure measurements, and then removed. Going forward, the calibration measurements are used, along with a change in PAT, to determine the patient's blood pressure and blood pressure variability. PAT typically relates inversely to blood pressure, i.e., a decrease in PAT indicates an increase in blood pressure.

A number of U.S. Patents and patent applications describe the relationship between PAT and blood pressure. For example, U.S. Pat. Nos. 5,316,008; 5,857,975; 5,865,755; and 5,649,543 each describe an apparatus that includes conventional sensors that measure ECG and PPG waveforms, which are then processed to determine PAT. PAT has been identified as promising surrogate for comfortable quasi-continuous and non-invasive BP monitoring [1-3]. Calibration steps are typically necessary to successfully estimate absolute BP from PAT, which have to be robust in terms of significant changes of the cardio-vascular status.

While the most common embodiment for measuring PAT is based on a simultaneous detection of an ECG waveform and a PPG waveform measured from the periphery, the measured time difference is the sum of the true vascular transit time (VTT), i.e. the time interval required for the pulse to propagate from the heart to the PPG sensor location, and the pre-ejection period (PEP), which is not related to pulse propagation. Proença et al., $32^{nd}$ Ann. Intl Conf. of the IEEE EMBS, 598-601, describe a study of the relation of PTT to BP measured by two different methods during physical exercise of healthy young subjects. One method is based on subtracting PEP from PAT, where PEP is provided from impedance cardiography. The second approach derives a VTT using two PPG sensors with one sensor positioned at the earlobe and the other at a finger. The results were said to suggest that neither method was good at monitoring blood pressure changes during exertion, and suggested that obtaining PEP through the ICG provides great uncertainties which have strong impact on VTT estimation, and that a PEP-free VTT derived by using a two PPG setup exhibited a poor correlation to SBP.

SUMMARY OF THE INVENTION

It is an object of the present invention to provide methods and systems for continuous noninvasive measurement of vital signs such as blood pressure (cNIBP) based on PAT, which features a number of improvements over conventional PAT measurements. The invention uses a body-worn monitor that recursively determines an estimated PEP for use in correcting PAT measurements by detecting low frequency vibrations created during a cardiac cycle, and using a state estimator algorithm to identify signals indicative of aortic valve opening in those measured vibrations. An uncorrected PAT is determined conventionally from the onset of the cardiac cycle and the time at which the corresponding pressure pulse is identified using pulse oximetry. PEP is then determined for each cardiac cycle on a beat-to-beat basis based on the difference between onset of the cardiac cycle (determined from an ECG sensor) and the currently estimated time of aortic valve opening. Using these values, a cNIBP measurement is obtained following correction of the PAT for PEP. Various vital signs obtained from such a body-worn system of sensors may be transmitted to a remote monitor, such as a tablet PC, workstation at a nursing station, personal digital assistant (PDA), or cellular telephone.

In a first aspect, the invention relates to methods of obtaining a continuous measurement of cardiac pre-ejection period for an individual for a plurality of cardiac cycles occurring over a time n, where n comprises a plurality of contractions c of the individual's heart. These methods comprise:
  acquiring a time-dependent electrocardiogram waveform using a first body-worn sensor apparatus configured to detect signals indicative of electrical activity of the individual's heart for time n;
  acquiring a time-dependent vibration waveform using a second body-worn sensor apparatus configured to detect signals indicative of vibrations having a frequency between 5 and 35 Hz caused by compression waves produced due to contraction of the individual's heart for time n;
  transmitting the time-dependent electrocardiogram waveform and the time-dependent vibration waveform to a processing apparatus; and
  processing the time-dependent electrocardiogram waveform and the time-dependent vibration waveform with the processing apparatus by
    (i) time synchronizing the time-dependent electrocardiogram waveform and the time-dependent vibration waveform,
    (ii) recursively determining an estimated time of aortic valve opening for each contraction c of the individual's heart during time n by processing the time-dependent vibration waveform using a state estimator algorithm which segments the time-dependent vibration waveform into a moving time window of length l comprising a plurality of contractions of the individual's heart which includes contraction c, and calculates the estimated time of aortic valve opening for contraction c from the data within the predetermined moving window, and
    (iii) recursively determining a pre-ejection period (PEP) for each contraction c of the individual's heart during time n by determining a time difference between a fiducial point in the time-dependent electrocardiogram waveform indicating the onset of electrical stimulation of the ventricles during contraction c and the estimated time of aortic valve opening determined for contraction c.

The phrase "time synchronizing" as used herein with regard to multiple sensor nodes, each generating a time-dependent waveform, refers to correlating the data from each node to a common timing clock. See, e.g., Elson et al., Fine-Grained Network Time Syncrhonization using Reference Broadcasts. In Proc. 5th Symp. Op. Syst. Design Implementation (OSDI), Boston, Mass., 2002; Elson and Romer. Wireless Sensor Networks: A New Regime for Time Synchronization. In Proc. First Workshop on Hot Topics In Networks (HotNets-I), Princeton, N.J., 2002.

The phrase "state estimator algorithm" as used herein refers to an algorithm that uses a series of measurements observed over time, containing noise (random variations) and other inaccuracies, and produces estimates of unknown variables that tend to be more precise than those based on a single measurement alone. By way of example only, a Kalman filter operates recursively on streams of noisy input data to produce a statistically optimal estimate of the underlying system state. In the prediction step, the Kalman filter produces estimates of the current state variables, along with their uncertainties. Once the outcome of the next measurement (necessarily corrupted with some amount of error, including random noise) is observed, these estimates are updated using a weighted average, with more weight being given to estimates with higher certainty. Because of the algorithm's recursive nature, it can run in real time using only the present input measurements and the previously calculated state and its uncertainty matrix; no additional past information is required. This is not meant to be limiting, as other state estimator algorithms are known in the art which may find use in the present invention. These include, but are not limited to, a boxcar filter, a Wiener filter, a minimum mean square error (MMSE) estimator, a recursive least squares estimator, a double exponential smoothing estimator, and/or a multi-fractional order estimator.

The phrase "fiducial point" refers to repeating landmarks within a waveform indicative of a recurring event. In addition to aortic valve opening, other fiducial points in the cardiac cycle include aortic valve closure, mitral valve closure, etc., and the time of each of these events may be extracted from the waveforms recorded in the present methods. As described hereinafter, compression waves produced due to contraction of the individual's heart may be recorded as low frequency (between 5 and 35 Hz) vibrations using sensors which detect acoustic and/or accelerometric sensors. In the case of accelerometry, such methods are known as seismocardiography, and the waveform is known as a ballistocardiogram or a seismocardiogram. See, e.g., Castiglioni et al., Conf Proc IEEE Eng Med Biol Soc. 2007; 2007:3954-7.

As described herein, the present methods are preferably configured to operate continually over a time n, where n comprises a plurality of cardiac cycles. For purposes of this invention, such a method is referred to as "continuous" operation. In preferred embodiments, n is at least 15 minutes, preferably at least 30 minutes, more preferably at least one hour, and most preferably at least 4 hours or more.

As also described herein, the present invention uses a sliding window of time to divide the time-dependent vibration waveform into a moving time window of length l comprising a plurality of contractions of the individual's heart. In preferred embodiments, this pre-determined moving window is between 15 seconds and 2 minutes. As described hereinafter, window length l may vary over time, such that when input data exhibits a low variance, the window is shortened, and when input data exhibits a higher variance, the window is lengthened.

Many of the waveforms used in the present claims are sensitive to motion or have a poor signal-to-noise ratio. Thus, the estimator algorithm acts to recursively provide an average measurement of PEP, a PAT, etc., over a time m; for a particular cardiac cycle, the currently measured average PEP, PAT, etc., may be used as the value of that particular parameter for the particular cardiac cycle. By way of example, a cardiac cycle may occur every 1 second, and an average PEP may be calculated over 10 cardiac cycles and updated every 0.5 seconds. At the time of any particular cardiac cycle, the average PEP at that instant may be used as the PEP form that cycle. In preferred embodiments, an average pre-ejection period ($m_{PEP}$) is calculated every m seconds from the PEPs determined for each contraction c during a time window w immediately preceding calculating $m_{PEP}$, wherein m is between 1 and 10 seconds, and w is between 15 seconds and 3 minutes.

Additionally, because the waveforms used in the present claims are sensitive to motion or have a poor signal-to-noise ratio, signal metrics may be utilized to discard particularly corrupted signal time windows. By way of example only, a median of the PEPs ($MED_{PEP}$) and a variance of the PEPs ($\sigma^2_{PEP}$) within time window w may be calculated, and PEPs determined for each contraction c during time window w which differ from $MED_{PEP}$ by more than $1\sigma$, more preferably $2\sigma$ or more, may be discarded prior to calculating $m_{PEP}$.

Because measured PAT is the sum of the true PAT (referred to herein as vascular transit time or VTT) and the PEP, PEP (either a single PEP measurement or more preferably average PEP ($m_{PEP}$) can be used to derive the VTT interval on a beat-by-beat basis. In certain embodiments, the present methods comprise acquiring a time-dependent plethysmogram waveform using a third body-worn sensor apparatus configured to detect signals indicative of changes in blood volume at an extremity produced due to contraction of the individual's heart for time n; and transmitting the time-dependent plethysmogram waveform to the processing apparatus, in order to provide a measured PAT.

In certain embodiments, the processing steps of the present methods further comprise:
(iv) time synchronizing the time-dependent plethysmogram waveform with the time-dependent electrocardiogram waveform and the time-dependent vibration waveform, and
(v) recursively determining a Pulse Arrival Time (PAT) for each contraction c of the individual's heart during time n by determining a time difference between a fiducial point in the time-dependent electrocardiogram waveform indicating the onset of electrical stimulation of the ventricles during contraction c and a fiducial point in the time-dependent plethysmogram waveform indicating arrival of the pressure wave at the extremity due to contraction c.

In certain embodiments, the processing further comprises recursively calculating an average PAT ($m_{PAT}$) every p seconds from the PATs determined for each contraction c during a time window q, wherein p is between 1 and 10 seconds, and q is between 15 seconds and 3 minutes; and a median of the PATs ($MED_{PAT}$) and a variance of the PATs ($\sigma^2_{PAT}$) within time window w may be calculated, and PATs determined for each contraction c during time window q which differ from $MED_{PEP}$ by more than $1\sigma$, more preferably $2\sigma$ or more, may be discarded prior to calculating $m_{VTT}$.

For convenience, m=p and w=q; however, these parameters need not be equal when, for example, $\sigma^2_{PEP}$ is substantially different than $\sigma^2_{PEP}$.

In various embodiments, the processing steps further comprise calculating a vascular transit time (VTT) for each contraction c during time n by subtracting $m_{PEP}$ at time t from $m_{PAT}$ at time t., and optionally calculating a blood pressure value using the VTT.

In a related aspect, the present invention relates to a system for obtaining a continuous measurement of cardiac pre-ejection period for an individual for a plurality of cardiac cycles occurring over a time n, where n comprises a plurality of contractions c of the individual's heart. These systems comprise:
   a first body-worn sensor apparatus configured to be worn on the patient's body and detect signals indicative of electrical activity of the individual's heart for time n and generate therefrom a time-dependent electrocardiogram waveform;
   a second body-worn sensor apparatus configured to be worn on the patient's body and detect signals indicative of vibrations having a frequency between 5 and 35 Hz caused by compression waves produced due to contraction of the individual's heart for time n and generate therefrom a time-dependent vibration waveform; and
   a processing apparatus operably connected to the first body-worn sensor and the second body-worn sensor, the processing apparatus configured to receive the time-dependent electrocardiogram waveform and the time-dependent vibration waveform, and to
      (i) time synchronize the time-dependent electrocardiogram waveform and the time-dependent vibration waveform,
      (ii) recursively determine an estimated time of aortic valve opening for each contraction c of the individual's heart during time n by processing the time-dependent vibration waveform using a state estimator algorithm which segments the time-dependent vibration waveform into a moving time window of length l comprising a plurality of contractions of the individual's heart which includes contraction c, and calculates the estimated time of aortic valve opening for contraction c from the data within the pre-determined moving window, and
      (iii) recursively determine a pre-ejection period (PEP) for each contraction c of the individual's heart during time n by determining a time difference between a fiducial point in the time-dependent electrocardiogram waveform indicating the onset of electrical stimulation of the ventricles during contraction c and the estimated time of aortic valve opening determined for contraction c.

In certain embodiments, the state estimator algorithm comprises a Kalman filter, a boxcar filter, a Wiener filter, a recursive least squares estimator, a double exponential smoothing estimator, a minimum mean square error (MMSE) estimator, and/or a multi-fractional order estimator. As noted above, this list is not meant to be limiting.

In certain embodiments the processing apparatus is further configured to recursively determine an estimated time of aortic valve closure for each contraction c of the individual's heart during time n using the state estimator algorithm.

In certain embodiments the processing apparatus is further configured to recursively determine an estimated time of mitral valve closure for each contraction c of the individual's heart during time n using the state estimator algorithm.

In certain embodiments the processing apparatus is further configured to recursively calculate an average pre-ejection period ($m_{PEP}$) every m seconds from the PEPs determined for each contraction c during a time window w immediately preceding calculating $m_{PEP}$, wherein m is between 1 and 10 seconds, and w is between 15 seconds and 3 minutes.

In certain embodiments a median of the PEPs ($MED_{PEP}$) and a variance of the PEPs ($\sigma^2_{PEP}$) within time window w are calculated by the processing system, and PEPs determined for each contraction c during time window w which differ from $PEP_{MED}$ by more than $2\sigma$ are discarded prior to calculating $m_{PEP}$.

In certain embodiments the system further comprises a third body-worn sensor apparatus configured to be worn on the patient's body and detect signals indicative of changes in blood volume at an extremity produced due to contraction of the individual's heart for time n and generate therefrom a time-dependent plethysmogram waveform. In preferred embodiments the third body-worn sensor apparatus is configured to be worn at the base of the patient's thumb or finger. In such embodiments the processing apparatus is preferably operably connected to the third body-worn sensor and is configured to (iv) time synchronize the time-dependent plethysmogram waveform with the time-dependent electrocardiogram waveform and the time-dependent vibration waveform, and (v) recursively determine a Pulse Arrival Time (PAT) for each contraction c of the individual's heart during time n by determining a time difference between a fiducial point in the time-dependent electrocardiogram waveform indicating the onset of electrical stimulation of the ventricles during contraction c and a fiducial point in the time-dependent plethysmogram waveform indicating arrival of the pressure wave at the extremity due to contraction c.

In certain embodiments the processing system is further configured to recursively calculate an average PAT ($m_{PAT}$) every p seconds from the PATs determined for each contraction c during a time window q, wherein p is between 1 and 10 seconds, and q is between 15 seconds and 3 minutes.

In certain embodiments a median of the PATs ($MED_{PAT}$) and a variance of the PATs ($\sigma^2_{PAT}$) within time window q are calculated by the processing system, and PATs determined for each contraction c during time window q which differ from $PAT_{MED}$ by more than $2\sigma$ are discarded prior to calculating $m_{VTT}$.

In certain embodiments the processing system is further configured to calculate a vascular transit time (VTT) for each contraction c during time n by subtracting $m_{PEP}$ at time t from $m_{PAT}$ at time t, and optionally to calculate a blood pressure value using the VTT.

DETAILED DESCRIPTION OF THE INVENTION

Measurement Overview

Figure 1A:
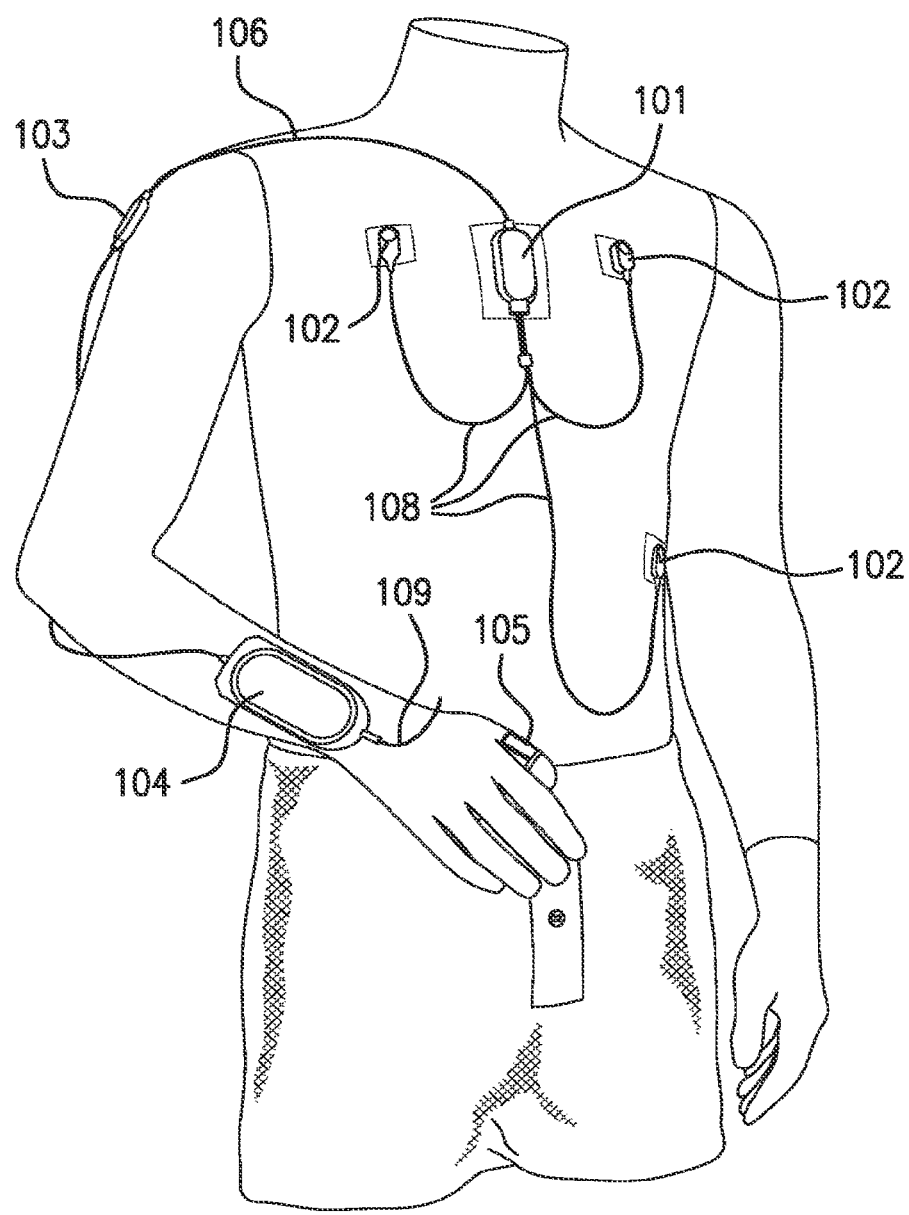
FIGS. 1A and 1B show an exemplary embodiment of the continuous vital sign measurement system of the present invention without (FIG. 1A) and with (FIG. 1B) a cuff-based oscillometric NIBP module.

The methods and systems described herein provide for continuous noninvasive measurement of vital signs such as blood pressure (cNIBP) based on PAT, which features a number of improvements over conventional PAT measurements. The invention uses a body-worn monitor that recursively determines an estimated PEP for use in correcting PAT measurements by detecting low frequency vibrations created during a cardiac cycle, and using a state estimator algorithm to identify signals indicative of aortic valve opening in those measured vibrations. As described below in an exemplary embodiment, a real-time cNIBP algorithm is described that utilizes a moving window to estimate blood pressure by combining timing measurements derived from ECG, SCG, and PPG waveforms. These timing measurements include PAT, PEP, and VTT. In these embodiments, a moving window is used to process the waveform data and provide continuous updates each cardiac cycle rather than batch processing the measurements from these waveforms.

Fiducial points derived from the SCG waveform are identified and used to adaptively compensate for changes in PEP that corrupt the PAT measurements used in the cNIBP algorithm. Signal averaging of the most recent cardiac cycle from the SCG waveform with multiple previous SCG cardiac cycles permit the algorithms to remove in-band noise and improve the distinction of physiologic features in the waveform. The SCG has a very poor signal-to-noise ratio (SNR) in some individuals, so this signal averaging the SCG provides an efficient way to significantly improve the SNR and the precision of PEP measurements As described hereinafter, applying a slope sum transformation to the signal averaged SCG waveform can help distinguish and select fiducial points in the current SCG waveform. The fiducial points include mitral valve closure, aortic valve opening, and aortic valve closure. Additionally, signal quality metrics (SQI's) derived from the SCG waveform and chest accelerometer are used to remove corrupted data from the SCG waveform prior to signal averaging the SCG waveform across multiple cardiac cycles. This reduces errors caused by motion artifact and minimizes variance in the measured PEP.

Similarly, SQI's derived from the PPG waveform and wrist accelerometer can be used to removed corrupted data values out of the calculation of a median PAT (or VTT) value. This reduces errors caused by motion artifact and minimizes variance in the measured PAT. Removing such corrupted waveform data prior to the median calculation is dramatically improves the measurement of cNIBP in a body worn device.

The present methods rely on use of a state estimator algorithm (exemplified as an adaptive Kalman filter) to determine improved mean and/or median PEP and PAT measurements that weights the update rate of the latest measurement based on the variance of the measurements in a moving time window. This update rate of the measurement can be fast when the variance in the moving window is small and slow when the variance in the moving window is large. This provides an efficient mechanism that allows cNIBP to react slowly or quickly to changes in PAT and/or VTT based on the variance.

Sensor Configurations

Figure 1B:
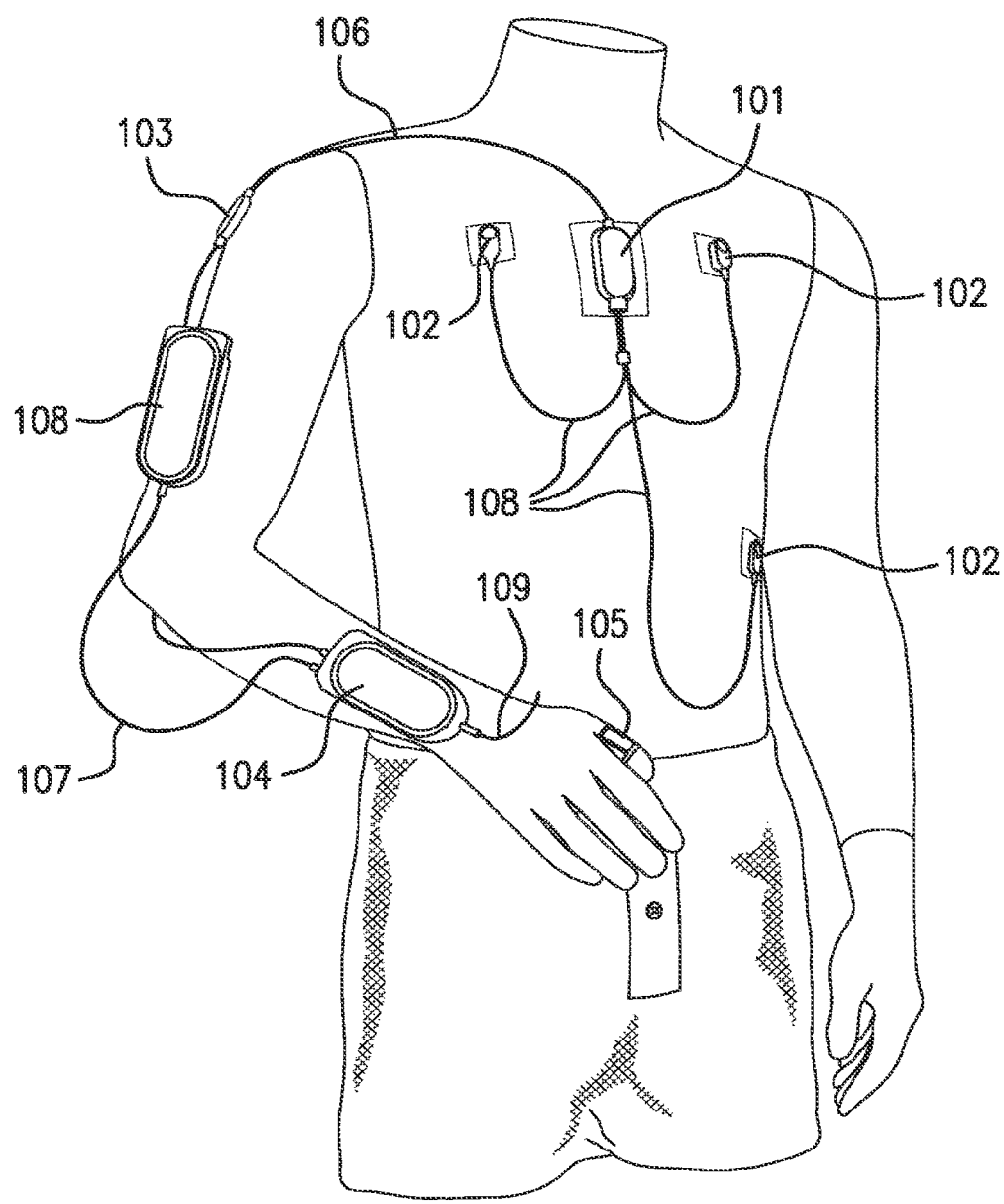

FIG. 1 depicts the system described herein as a cNIBP monitor consisting of an ECG/accelerometer module 101, a wrist transceiver/processing unit 104, a pulse oximetry module 105 and NIBP module 108 which determines an oscillometric blood pressure measurement. These device components are capable of measuring four different physiologic signals; an electrocardiogram (ECG), a photoplethysmogram (PPG), a vibrational waveform known as a seismocardiogram (SCG), and a brachial artery pressure signal that provides an oscillometric blood pressure measurement (NIBP).

The exemplified system comprises an ECG/accelerometer sensor module 101 that includes a housing enclosing (i) an ECG circuit operably connected to a transceiver within the housing that transmits ECG waveforms (e.g., using cable 106 or by wireless connection) to a corresponding transceiver housed within a processing apparatus 104; and (ii) an accelerometer (e.g., ADXL-345 or LSM330D) also operably connected to the transceiver within the housing that transmits accelerometer (SCG) waveforms to a corresponding transceiver housed within a processing apparatus 104. ECG/accelerometer sensor module 101 is positioned on the patient's skin at the sternum. While the ECG sensor module and the accelerometer module may be provided separately, it is advantageous for ease of use that a single housing 101 encloses both sensor modules. Similarly, while the processing apparatus 104 is depicted herein as a single body-worn processor unit, the algorithms described herein may be performed by a plurality of processors which may be housed at different locations, each of which contributes to the processing power of the system, and which are collectively therefore referred to as "the processing apparatus." By way of example only, a processing unit may be provided at the bedside or provided in a body-worn client/remote server processor format.

In order to achieve a sufficient signal-to-noise ratio for the SCG signal the ECG/accelerometer module 101 should be mechanically coupled to the patient's skin. The housing of the ECG/accelerometer module 101 is secured against the patient's skin using a double-sided adhesive substance applied directly between the housing and the skin or by snapping it into a rigid fixture that is adhered to the skin. The housing should be attached at the sternum of the patient, optimally the lower sternum just above the xiphoid process. The microprocessor component of transceiver/processing apparatus 104 applies algorithms as described below in order to collectively process ECG waveforms along with SCG waveforms to generate an improved PAT measurement.

The ECG circuit within the ECG/accelerometer module 101 features a single circuit (e.g. an ASIC) that collects electrical signals from a series of body-worn electrodes 102 and coverts these signals into a digital ECG waveform. Such a circuit connects to the wrist transceiver through a digital, serial interface (e.g. an interface based on a "controller area network", or "CAN", system). The chest-worn ECG/accelerometer module 101 connects through cables 108 to conventional ECG electrodes 102 located, respectively, in the upper right-hand, upper left-hand, and lower left-hand portions of the patient's thorax. Three electrodes 102 (two detecting positive and negative signals, and one serving as a ground) are typically required to detect the necessary signals to generate an ECG waveform with an adequate signal-to-noise ratio. RED DOT™ electrodes marketed by 3M (3M Center, St. Paul, Minn. 55144-1000) are suitable for this purpose. During a measurement, the ECG electrodes 102 measure analog signals that pass to circuits within the ECG/accelerometer module 101. There, ECG waveforms are generated, digitized (typically with 12-24-bit resolution and a sampling rate between 250-500 Hz), and formulated in individual packets so they can be transmitted to the wrist-worn transceiver/processing apparatus 104 for processing.

The individual packets described above may be preferably transmitted according to the controller area network (CAN) protocol. Use of this protocol with a wired or wireless connection between the ECG/accelerometer module 101 and wrist-worn transceiver/processing apparatus 104 provides packets in which all timing related information between the packets is preserved such that the waveforms generated by the ECG and accelerometer may be synchronized (optionally with PPG waveforms) by the wrist-worn transceiver/processing apparatus 104. The CAN protocol also permits the data corresponding to waveforms generated by the ECG and accelerometer to be segregated although transmitted by a single transceiver, as each packet can contain information designating the sensor from which the data originates.

The optical sensor 105 detects optical radiation modulated by the heartbeat-induced pressure wave, which is further processed with a second amplifier/filter circuit within the transceiver/processing apparatus 104. This results in the PPG waveform, which, as described above, includes a series of pulses, each corresponding to an individual heartbeat. The depicted thumb-worn optical sensor 105 is operably connected (wirelessly or through a cable 109 to the wrist-worn transceiver/processing apparatus 104 to measure and transmit PPG waveforms that, when combined with the ECG waveform, can be used to generate cNIBP measurements according to the algorithms described below. This yields individual blood pressure values (systolic or "SYS", diastolic or "DIA", and mean arterial or "MAP"). The optical sensor 105 additionally measures a PPG waveform that can be processed to determine SpO2 values, as described in detail in the following patent application, the contents of which are incorporated herein by reference: BODY-WORN PULSE OXIMETER, U.S. Ser. No. 12/559,379, filed Sep. 14, 2009.

In addition to the accelerometer located on the sternum within housing 101, the system comprises two other accelerometers; one positioned on the wrist within the wrist-worn transceiver/processing apparatus 104 and the other on the upper arm of the same arm 103. Each measures three unique signals, each corresponding to the x, y, and z-axes of the body portion to which the accelerometer attaches. These signals are then processed by the wrist-worn transceiver/processing apparatus 104 with a series of algorithms, some of which are described in the following patent application, the contents of which are incorporated herein by reference: BODY-WORN VITAL SIGN MONITOR WITH SYSTEM FOR DETECTING AND ANALYZING MOTION (U.S. Ser. No. 12/469,094; filed May 20, 2009) to determine motion, posture, arm height, and activity level.

Finally, the system further comprises a pneumatic cuff-based module 108 that communicates with the wrist-worn transceiver/processing apparatus 104 in order to obtain oscillometric NIBP measurements. The cuff module 108 features a pneumatic system that includes a pump, valve, pressure fittings, pressure sensor, analog-to-digital converter, microcontroller, transceiver, and rechargeable Li:ion battery. During an indexing measurement, the pneumatic system inflates a disposable cuff and performs two measurements: 1) an inflation-based measurement of oscillometry to determine values for $SYS_{INDEX}$, $DIA_{INDEX}$, and $MAP_{INDEX}$; and 2) a patient-specific slope describing the relationship between PTT and MAP. These measurements are described in detail in the above-referenced patent application entitled: 'VITAL SIGN MONITOR FOR MEASURING BLOOD PRESSURE USING OPTICAL, ELECTRICAL, AND PRESSURE WAVEFORMS' (U.S. Ser. No. 12/138,194; filed Jun. 12, 2008), the contents of which have been previously incorporated herein by reference. Pressure waveforms are transmitted by the transceiver to the wrist-worn transceiver/processing apparatus 104 (wirelessly or through cable 107) through a digital, serial interface, and preferably as packets according to the controller area network (CAN) protocol.

Summary of the Data Acquisition and Signal Filtering

ECG: Electrocardiogram signals may be sampled at a sampling frequency of 500 Hz. The ECG signals were digitally filtered using a high pass filter (−3 dB at 0.7 Hz) and a 60 Hz notch filter, digitized using an A/D converter contained within the ECG/accelerometer module 101, and transmitted as packet data to the wrist-worn transceiver/processing apparatus 104.

PPG: The photoplethysmogram signals were sampled by an analog to digital converter at a sampling frequency of 500 Hz. The PPG signals were digitally filtered using a low-pass filter (−3 dB at 10 Hz) and transmitted as analog data to the wrist-worn transceiver/processing apparatus 104 where the signals are digitized by an A/D converter within the wrist-worn transceiver/processing apparatus 104.

NIBP: The pressure transducer signals were sampled by an analog to digital converter at a sampling frequency of 500 Hz. The pressure signals were digitally filtered using a low-pass filter (−3 dB at 6 Hz), digitized using an A/D converter contained within the cuff module 108, and transmitted as packet data to the wrist-worn transceiver/processing apparatus 104.

SCG: The seismocardiogram signals were digitally captured at a sampling frequency of 500 Hz. The SCG signals were digitally filtered using a band-pass filter (−3 dB at 5 Hz and 35 Hz), digitized using an A/D converter contained within the ECG/accelerometer module 101, and transmitted as packet data to the wrist-worn transceiver/processing apparatus 104.

Measurement of PAT & VTT

The cNIBP measurement is based on the measurement of pulse wave velocity. The velocity of a pressure pulse as it travels along an arterial pathway is dependent on the distensibility of the arteries along the transit path. Distensibility is a function of the compliance and volume of the artery. The distensibility of an artery is dependent on the pressure acting across the arterial wall or transmural pressure. Typically the transmural pressure is equivalent to the arterial blood pressure hence the velocity of the pulse wave is a function of arterial pressure. Two different timing measurements, vascular transit time (VTT) and pulse arrival time (PAT) were used to quantify the velocity of the pressure pulse wave.

Figure 2:
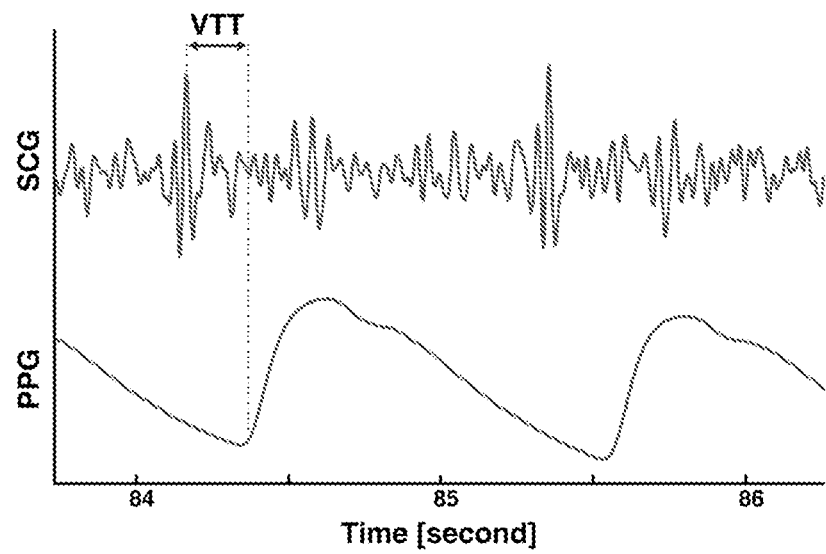
FIG. 2 shows exemplary seismocardiogram (SCG) and photoplethysmogram (PPG) waveforms obtained by the methods described herein, depicting exemplary fiducial points within the synchronized waveforms corresponding to vascular transit time (VTT).

VTT was measured on a beat-to-beat basis as the time difference between the onset of the photoplethysmogram at the base of the thumb (or finger) and the opening of the aortic valve measured by the accelerometer based seismocardiogram as shown in FIG. 2. The fiducial point used to represent the opening of the aortic valve in the SCG waveform was determined in the following manner.

Signal averaging: The SCG signal may contain noise within the frequency band of our band-pass filter (5 Hz-35 Hz). A signal averaging technique can be used to remove this noise prior to locating aortic valve opening. The SCG signal can be viewed as the response to the mechanical activity of the heart during each cardiac cycle. The duration of a cardiac cycle can be defined as the time between adjacent peaks of the QRS cycle in the ECG or RR interval. The signal averaged SCG waveform corresponding to each cardiac cycle is defined using the sample numbers of the R-peaks ($R_{peak}[i]$) as given in equation (1). The length variable L, corresponds to the median number of samples in the RR intervals within the last N cardiac cycles.

$$SCG[R_{peak}[i] + j] = \frac{1}{N} \sum_{k=i-N-1}^{i} SCG[R_{peak}[k] + j] \text{ for } 0 \leq j < L \quad (1)$$

Waveform transformation: In order to accentuate features in the filtered SCG waveform for automated detection every sample of the filtered SCG waveform for each cardiac cycle is transformed into a slope sum waveform (SSF) as given in equations (2), (3), and (4) where length M is selected to accentuate the features corresponding to the opening of the aortic valve.

$$\frac{dSCG[i]}{dt} = SCG[i] - SCG[i-1] \quad (2)$$

$$\text{if } \frac{dSCG[i]}{dt} > 0 \text{ then } \frac{dSCG[i]}{dt} = 0 \quad (3)$$

$$SSF[i] = \sum_{i-M}^{i} \frac{dSCG[i]}{dt} \quad (4)$$

The two negative peaks with largest absolute magnitude in the SSF waveform for each cardiac cycle are identified using an adaptive threshold to eliminate noise and other small magnitude vibrations.

The peak of the filtered SCG waveform that lies between the two negative slope sum peaks was determined as the fiducial point that defined the opening of the aortic valve.

The VTT value was considered to be valid and used by the blood pressure algorithm if the delay between the SCG fiducial point and the peak of the ECG QRS complex fell within a specified range [75 ms 175 ms], and if the VTT value was within a valid range [30 ms 300 ms].

Figure 3:
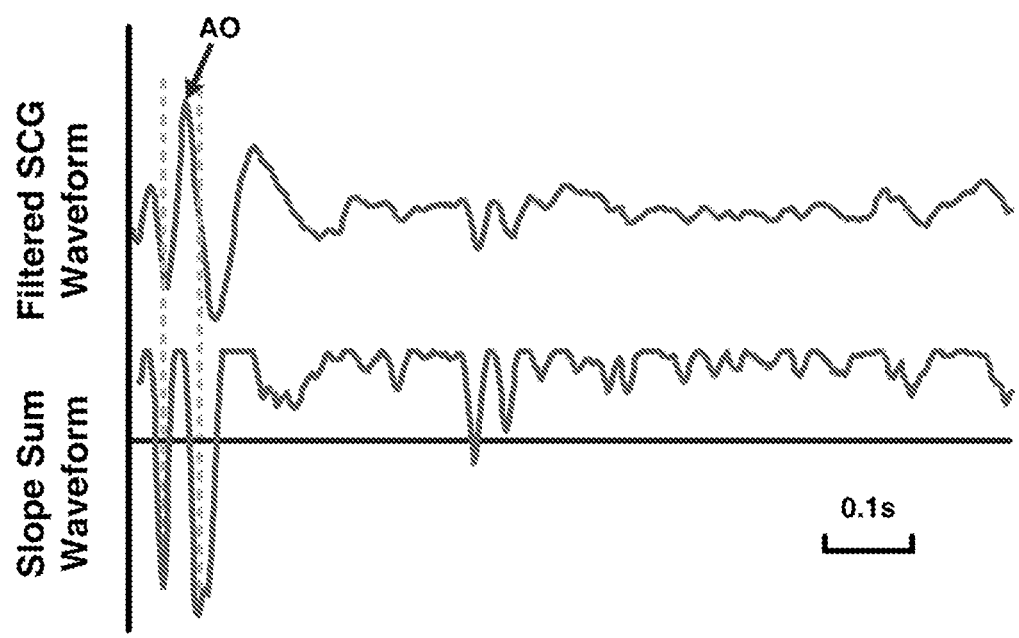
FIG. 3 shows an exemplary seismocardiogram (SCG) which has been band-pass filtered to 5 Hz-35 Hz and signal averaged within a time window, and a corresponding transformation of this waveform by slope sum transformation.

The filtered SCG waveform and slope sum waveform are shown in FIG. 3 along with the adaptive threshold and the fiducial points selected to represent the opening of the aortic valve.

Figure 4:
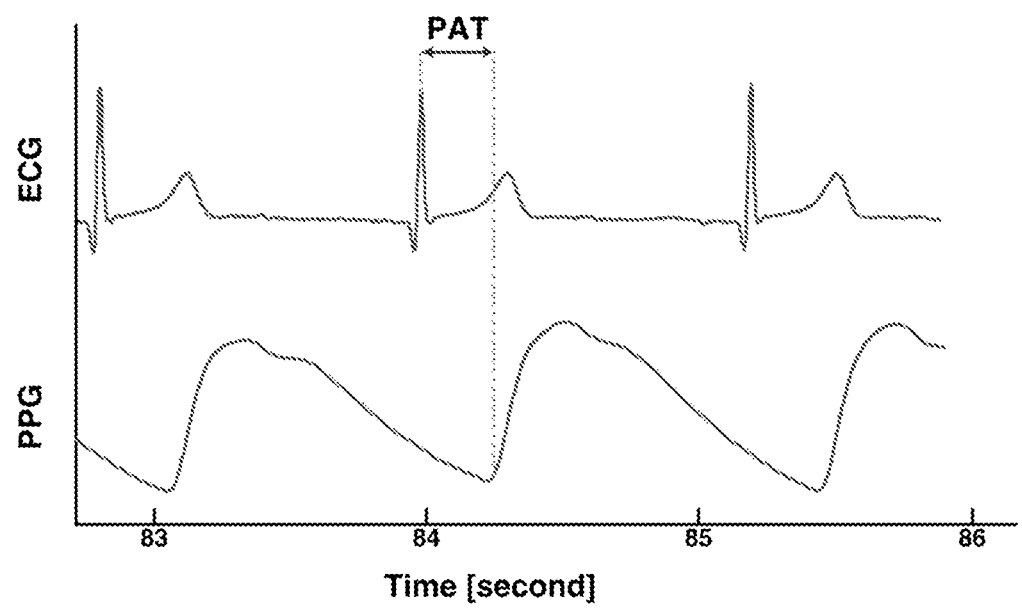
FIG. 4 shows exemplary electrocardiogram (ECG) and photoplethysmogram (PPG) waveforms obtained by the methods described herein, depicting exemplary fiducial points within the synchronized waveforms corresponding to pulse arrival time (PAT).

PAT was measured on a beat-to-beat basis as the time difference between the onset of the photoplethysmogram at the base of the thumb (or index finger) and the peak of the QRS complex in the ECG waveform as shown in FIG. 4.

Blood Pressure Estimation with Vascular Transit Time

Continuous blood pressure measurements were determined directly from the vascular transit time measurements calculated from the seismocardiogram and photoplethysmogram. A summary of the method is provided below.

Step 1) Calibrate VTT to Blood Pressure with the NIBP Cuff Inflation

In order to calculate blood pressure using VTT a model was identified to characterize the relationship between VTT and mean arterial blood pressure (MAP) as given in equation (5) where $L_t$ represents the length of the arterial transit path between the aortic valve and the site of the optical sensor.

$$VTT = \left(\frac{L_t}{pwv}\right) = \left(\frac{L_t}{aMAP + pwv_0}\right) \quad (5)$$

The model parameters (a and $pwv_0$) were identified using the NIBP module to create a unique calibration for each subject.

During cuff inflation the increase in cuff pressure ($P_{cuff}$) causes a decrease in the transmural pressure ($P_{tm}$) acting across the brachial artery wall. An expression for the transmural pressure acting on the arterial segment under the cuff is given in equation (6) where the intravascular pressure is defined as the mean arterial pressure at the time of the inflation ($MAP_{cal}$).

$$P_{tm}(t) = MAP_{cal} - P_{cuff}(t) \quad (6)$$

As the transmural pressure acting on the brachial artery decreases with an increase in cuff pressure the compliance and distensibility of the artery increases. The increased distensibility decreases the velocity of the pressure pulse in this arterial segment thereby increasing the measured VTT. The expression used to describe the relationship between VTT, the mean arterial pressure measured by the NIBP module cal, ($MAP_{cal}$), and the pressure in the NIBP cuff ($P_{cuff}$) during inflation is given in equation (7) where $L_e$ represents the length of the brachial artery affected by the cuff.

$$VTT(t) = \left(\frac{L_t - L_c}{aMAP_{cal} + pwv_0}\right) + \left(\frac{L_c}{a(MAP_{cal} - P_{cuff}(t)) + pwv_0}\right) \quad (7)$$

The unknown parameter values (a and $pwv_0$) are identified from the VTT values and cuff pressures measured during the NIBP inflation period by minimizing the squared error between the measured and estimated VTT using the Levenberg-Marquardt algorithm.

Additionally, inflation of the NIBP cuff provides an oscillometric blood pressure measurement for systolic pressure ($SYS_{cal}$), diastolic pressure ($DIA_{cal}$), and mean arterial pressure ($MAP_{cal}$) at the time of the inflation.

The unique patient ratio used to estimate diastolic pressure ($R_{dia}$) in the cNIBP algorithm is calculated based on the oscillometric blood pressure measurements as given in equation (8).

$$R_{dia} = \left(\frac{DIA_{cal}}{MAP_{cal}}\right) \quad (8)$$

The unique patient ratio used to estimate systolic pressure ($R_{sys}$) in the cNIBP algorithm is calculated based on the oscillometric blood pressure measurements as given in equation (9).

$$R_{sys} = \left(\frac{SYS_{cal}}{MAP_{cal}}\right) \quad (9)$$

Step 2) Calculate an Aggregate VTT

Vascular transit time values are measured on a beat-by-beat basis however signal artifact in the SCG and PPG due to motion or other sources of corruption will cause significant error in these real-time measurements particularly for a patient worn monitor. Additionally, physiologic phenomenon such as thoracic pressure change due to respiration cause variation in VTT on a beat-by-beat basis. The cNIBP determination employees a multi-step algorithm to remove spurious VTT measurements and provide an aggregated VTT value to calculate an accurate blood pressure.

Beat-to-beat VTT values were classified as rejected or accepted based on several screening criteria. A VTT value was rejected if a patient's motion exceeded a fixed threshold. The magnitude of patient motion was measured by accelerometers located in the wrist transceiver and ECG module. Additionally VTT values were classified using several signal quality indices (SQI's) derived from the PPG signal. The PPG SQI's were determined from the PPG pulse used to identify the onset point for the VTT measurement. A VTT value was classified as rejected if the SQI's exhibited variance above a predefined threshold. The VTT values were also classified using several SQI's derived from the SCG signal. The SQI's were determined from the SCG signal for the cardiac cycle used to determine when the aortic valve opened. A VTT value was classified as rejected when the SQI's exhibited variance above a predefined threshold.

An aggregate VTT value was calculated periodically (every 3 seconds) from all of the VTT measurements collected in the 60-second period prior to the update time.

The first step used to determine an aggregate VTT value was to calculate a mean VTT value ($m_1$) and the standard deviation ($\sigma_1$) of the VTT values in the 60-second window for all measurements that were classified as accepted.

The second step in the process was to calculate a median VTT value ($MED_{VTT}$) and the variance of the VTT values ($\sigma^2_{VTT}$) in the 60-second window using VTT measurements that were screened as accepted and VTT values that were inside an upper bound ($m_1 + 2\sigma_1$) and lower bound ($m_1 - 2\sigma_1$) defined using the mean and standard deviation calculated in step 1 of the VTT aggregation.

The final step used to determine an aggregate VTT value for each periodic update was to apply an adaptive moving average filter to the median VTT value from step 2 and the previous aggregated VTT value. The adaptive filter utilizes the framework of a Kalman filter to calculate a gain that was applied to the difference between the new median VTT value and the previous aggregated VTT value. The Kalman filter allows us to increase the response rate of the cNIBP monitor to a change in VTT when our confidence in the new median value is high and decreases the cNIBP response rate to VTT change when our confidence in the new median value is low. The procedure used to determine the aggregated VTT numeric value ($VTT_{num}$) with the adaptive filter is given below.

Calculate the a priori error covariance ($P_{pri}$) given the previous estimate or an initial estimate of the posteriori error variance ($P_{post}$), the VTT variance calculated in step 2, and the state transition matrix A.

$$P_{pri} = A \cdot P_{post} \cdot A^T + \sigma_{VTT}^2 \quad (10)$$

Calculate the Kalman Gain (G) given the output matrix (H) and a pre-defined PAT process variance ($R_{VTT}$).

$$G = P_{pri} \cdot H^T \cdot (H \cdot P_{pri} \cdot H^T + R_{VTT})^{-1} \quad (11)$$

Calculate the a priori state estimate ($x_{pri}$) based on the posteriori state estimate ($x_{post}$) and state transition matrix A.

$$x_{pri} = A \cdot x_{post} \quad (12)$$

Update the posteriori state estimate using the median VTT value and the Kalman gain (G).

$$x_{post} = x_{pri} + G \cdot (MED_{VTT} - H \cdot x_{pri}) \quad (13)$$

The aggregate VTT numeric ($VTT_{num}$) value can be defined in terms of the output matrix (H) and the posteriori state estimate ($x_{post}$)

$$VTT_{num} = H \cdot x_{post} \quad (14)$$

Prior to the next periodic calculation the error covariance ($P_{post}$) was updated.

$$P_{post} = (I - G \cdot H) \cdot P_{pri} \quad (15)$$

The simplest implementation of this filter is one that defines A=H=1. In this case the implementation can be reduced to 3 equations.

$$G = (P_{post} + \sigma_{VTT}^2) / (P_{post} + \sigma_{VTT}^2 + R_{VTT}) \quad (16)$$

$$VTT_{num}(t) = VTT_{num}(t-3 \text{ sec}) + G \cdot (VTT_{num}(t-3 \text{ sec}) - VTT_{med}) \quad (16)$$

$$P_{post} = (1-G) \cdot (P_{post} + \sigma_{VTT}^2) \quad (17)$$

Step 3) Calculate Blood Pressure

Values for systolic, diastolic, and mean arterial pressure are determined for every aggregate VTT value calculated in the previous step using the formulas given in equations (18), (19), and (20) where $VTT_{cal}$ represents an aggregate VTT measured at the time of the NIBP inflation.

$$MAP = \left(\frac{L_t}{a}\right)\left(\frac{1}{VTT_{num}} - \frac{1}{VTT_{cal}}\right) + MAP_{cal} \quad (18)$$

$$SYS = R_{sys} \cdot MAP \quad (19)$$

$$DIA = R_{dia} \cdot MAP \quad (20)$$

Correction for Pre-Ejection Period Changes Using the Seismocardiogram

In addition to providing a measure of vascular transit time the SCG signal can be used to measure the duration of the cardiac pre-ejection period. The pre-ejection period (PEP) is the combination of the electromechanical delay of the heart and the period of isovolumic contraction of the left ventricle prior to the opening of the aortic valve. PEP can be measured as the time difference between the opening of the aortic valve in the SCG waveform and the peak of the QRS cycle in the ECG waveform.

Pulse arrival time is the time difference between the onset of the PPG waveform and the peak of the QRS cycle in the ECG. Due to the ECG's high signal to noise ratio and its motion tolerance it can provide a more robust means to determine beat to beat changes in pulse wave velocity compared to using the SCG to calculate VTT. Therefore continuous non-invasive blood pressure can be calculated directly from pulse arrival time.

However, in addition to capturing changes in pulse wave velocity the PAT values also track changes in PEP that may be uncorrelated with changes in arterial blood pressure. The PEP measured by the SCG waveform can be used to identify and compensate for changes in PAT that are induced by changes in PEP. This strategy allows PEP values measure from an SCG signal with poor signal to noise ratio to use a longer averaging window without sacrificing the cNIBP monitors response to changes in arterial pressure measured with PAT.

The procedure used to make cNIBP measurements with PAT while correcting for changes in PEP using an accelerometer-based seismocardiogram is outlined below.

Step 1) Calibrate PAT to Blood Pressure with the NIBP Cuff Inflation

The algorithm used to identify a calibration equation between PAT and MAP using the NIBP inflation is analogous to the procedure described for VTT in the previous section except that VTT measurements are replaced with PAT measurements as given in equation (21).

$$PAT = \left(\frac{L_t}{pwv}\right) = \left(\frac{L_t}{aMAP + pwv_0}\right) \quad (21)$$

The model parameters (a and $pwv_0$) were identified using the NIBP module to create a unique calibration for each subject.

Step 2) Calculate an Aggregate PAT, PEP, and cPAT

PAT values and PEP values are measured on a beat-by-beat basis however signal artifact in the ECG, PPG, and SCG due to motion or other sources of corruption will cause significant error in these real-time measurements particularly for a patient worn monitor. The ViSi cNIBP monitor employees a multi-step algorithm to remove spurious PAT and PEP measurements and provide aggregated PAT and PEP values to calculate blood pressure.

Beat-to-beat PAT values were classified as rejected or accepted based on several screening criteria. A PAT value was rejected if a patient's motion exceeded a fixed threshold. The magnitude of patient motion was measured by an accelerometer located in the wrist transceiver. Additionally PAT values were classified using several SQI's derived from the PPG signal. The SQI's were determined from the PPG pulse used to identify the onset point. When the SQI's exhibited variance above a predefined threshold the PAT value was classified as rejected if it was below the threshold it was accepted.

Beat-to-beat PEP values were also classified as rejected or accepted based on several screening criteria. A PEP value was rejected if a patient's motion exceeded a fixed threshold. The magnitude of patient motion was measured by an accelerometer located in the ECG module. Additionally PEP values were classified using several SQI's derived from the SCG signal. The SQI's were determined from the SCG signal for the cardiac cycle used to determine when the aortic valve opened. When the SQI's exhibit variance above a predefined threshold the PEP value was classified as rejected if it was below the threshold it was accepted.

An aggregate PAT value was calculated periodically (every 3 seconds) from all of the PAT measurements collected in the 60-second period prior to the update time. The first step used to determine an aggregate PAT value was to calculate a mean PAT value ($m_1$) and the standard deviation ($\sigma_1$) of the PAT values in the 60-second window for all measurements that were classified as accepted.

The second step in the process was to calculate a median PAT value ($PAT_{med}$) and the variance of the PAT values ($\sigma^2_{PAT}$) in the 60-second window using PAT measurements that were screened as accepted and PAT values that were inside an upper bound ($m_1 + 2\sigma_1$) and lower bound ($m_1 - 2\sigma_1$) defined using the mean and standard deviation calculated in step 1 of the PAT aggregation.

The final step used to determine an aggregate PAT value for each periodic update was to apply an adaptive moving average filter to the median PAT value from step 2 and the previous aggregated PAT value. The adaptive filter utilizes the framework of a Kalman filter to calculate a gain that was applied to the difference between the new median PAT value and the previous aggregated PAT value. The Kalman filter allows us to increase the response rate of the cNIBP monitor to a change in PAT when our confidence in the new median value is high and decrease the cNIBP response rate to PAT change when our confidence in the new median value is low. The procedure used to determine the aggregated PAT numeric value ($PAT_{num}$) with the adaptive filter is given below.

Calculate the a priori error covariance ($P_{pri}$) given the previous estimate or an initial estimate of the posteriori error variance ($P_{post}$), the PAT variance calculated in step 2, and the state transition matrix A.

$$P_{pri} = A \cdot P_{post} \cdot A^T + \sigma_{PAT}^2 \quad (22)$$

Calculate the Kalman Gain (G) given the output matrix (H) and a pre-defined PAT process variance ($R_{PAT}$).

$$G = P_{pri} \cdot H^T \cdot (H \cdot P_{pri} \cdot H^T + R_{PAT})^{-1} \quad (23)$$

Calculate the a priori state estimate ($x_{pri}$) based on the posteriori state estimate ($x_{post}$) and state transition matrix A.

$$x_{pri} = A \cdot x_{post} \quad (24)$$

Update the posteriori state estimate using the median PAT value and the Kalman gain (G).

$$x_{post} = x_{pri} + G \cdot (PAT_{med} - H \cdot x_{pri}) \quad (25)$$

The aggregate PAT numeric ($PAT_{num}$) value can be defined in terms of the output matrix (H) and the posteriori state estimate ($x_{post}$)

$$PAT_{num} = H \cdot x_{post} \quad (26)$$

Prior to the next periodic calculation the error covariance ($P_{post}$) was updated.

$$P_{post} = (I - G \cdot H) \cdot P_{pri} \quad (27)$$

The simplest implementation of this filter is one that defines A=H=1. In this case the implementation can be reduced to 3 equations.

$$G = (P_{post} + \sigma_{PAT}^2) / (P_{post} + \sigma_{PAT}^2 R_{PAT}) \quad (28)$$

$$PAT_{num}(t) = PAT_{num}(t-3 \text{ sec}) + G \cdot (PAT_{num}(t-3 \text{ sec}) - PAT_{med}) \quad (29)$$

$$P_{post} = (1 - G) \cdot (P_{post} + \sigma_{PAT}^2) \quad (30)$$

An aggregate PEP value was calculated periodically (every 3 seconds) from all of the PEP measurements collected in the 60-second period prior to the time of the update.

The first step used to determine an aggregate PEP value was to calculate a mean PEP value ($m_1$) and the standard deviation ($\sigma_1$) of the PEP values in the 60-second window for all measurements that were classified as accepted.

The second step in the process was to calculate a median PEP value ($PEP_{med}$) and the variance of the PEP values ($\sigma^2_{PEP}$) in the 60-second window using PEP measurements that were screened as accepted and PEP values that were inside an upper bound ($m_1 + 2\sigma_1$) and lower bound ($m_1 - 2\sigma_1$) defined using the mean and standard deviation calculated in step 1 of the PEP aggregation.

The final step used to determine an aggregate PEP value for each periodic update was to apply an adaptive moving average filter to the median PEP value from step 2 and the aggregated PEP value from the prior 3-second update. The adaptive filter utilizes the framework of a Kalman filter to calculate a gain that was applied to the difference between the new median PEP value and the previous aggregated PEP value. The Kalman filter allows us to increase the response rate of the PEP measurement when our confidence in the new median is high and decreases the response rate to PEP change when our confidence in the new median value is low. The procedure used to determine the aggregated PEP numeric value ($PEP_{num}$) with the adaptive filter is given below.

Calculate the a priori error covariance ($P_{pri}$) given the previous estimate or an initial estimate of the posteriori error variance ($P_{post}$), the PEP variance calculated in step 2, and the state transition matrix A.

$$P_{pri} = A \cdot P_{post} \cdot A^T + \sigma_{PEP}^2 \quad (31)$$

Calculate the Kalman Gain (G) given the output matrix (H) and a pre-defined PEP process variance ($R_{PEP}$).

$$G = P_{pri} \cdot H^T \cdot (H \cdot P_{pri} \cdot H^T + R_{PEP})^{-1} \quad (32)$$

Calculate the a priori state estimate ($x_{pri}$) based on the posteriori state estimate ($x_{post}$) and state transition matrix A.

$$x_{pri} = A \cdot x_{post} \quad (33)$$

Update the posteriori state estimate using the median PEP value and the Kalman gain (G).

$$x_{post} = x_{pri} + G \cdot (PEP_{med} - H \cdot x_{pri}) \quad (34)$$

The aggregate PEP numeric ($PEP_{num}$) value can be defined in terms of the output matrix (H) and the posteriori state estimate ($x_{post}$)

$$PEP_{num} = H \cdot x_{post} \quad (35)$$

Prior to the next periodic calculation update the error covariance ($P_{post}$).

$$P_{post} = (I - G \cdot H) \cdot P_{pri} \quad (36)$$

A simple implementation of the adaptive filter is one that defines A=H=1. In this case the implementation can be reduced to 3 equations given below.

$$G = (P_{post} + \sigma_{PEP}^2) / (P_{post} + \sigma_{PEP}^2 + R_{PEP}) \quad (37)$$

$$PEP_{num}(t) = PEP_{num}(t-3 \text{ sec}) + G \cdot (PEP_{num}(t-3 \text{ sec}) - PEP_{med}) \quad (38)$$

$$P_{post} = (1 - G) \cdot (P_{post} + \sigma_{PEP}^2) \quad (39)$$

Step 3) Calculate Blood Pressure

The first step to determine a blood pressure value is to calculate a corrected PAT value (cPAT) using the latest aggregated PAT and PEP values as given in equation (40) where $PEP_{cal}$ represents an aggregate PEP measured at the time of the NIBP inflation.

$$cPAT = PAT_{num} - (PEP_{num} - PEP_{cal}) \quad (40)$$

Values for systolic, diastolic, and mean arterial pressure are determined for every cPAT value using the formulas given in equations (41), (42), and (43) where $PAT_{cal}$ represents an aggregate PAT measured at the time of the NIBP inflation.

$$MAP = \left(\frac{L_t}{a}\right)\left(\frac{1}{cPAT} - \frac{1}{PAT_{cal}}\right) + MAP_{cal} \quad (41)$$

$$SYS = R_{sys} \cdot MAP \quad (42)$$

$$DIA = R_{dia} \cdot MAP \quad (43)$$

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A system for obtaining a continuous measurement of cardiac pre-ejection period for an individual, comprising:
    an ECG sensor configured to be worn on the patient's body and detect signals indicative of electrical activity of the individual's heart for time n, filter the signals using a 60 Hz notch filter, digitize the filtered signals, generate therefrom a time-dependent electrocardiogram waveform, and transmit the time-dependent electrocardiogram waveform as packet data;
    a seismocardiogram sensor configured to be worn on the patient's body and detect signals indicative of compression waves produced due to contraction of the individual's heart for time n, filter the signals using a 5 and 35 Hz bandpass filter, digitize the filtered signals, generate therefrom a time-dependent seismocardiogram waveform, transmit the time-dependent seismocardiogram waveform as packet data; and
    a processing apparatus operably connected to the first body-worn sensor and the second body-worn sensor, the processing apparatus configured to receive the time-dependent electrocardiogram waveform transmitted by the ECG sensor and the time-dependent seismocardiogram waveform transmitted by the seismocardiogram sensor, and to
    (i) recursively determine the occurrence of aortic valve opening for each contraction c of the individual's heart during time n by processing a portion of the time-dependent seismocardiogram waveform within a moving time window of length l comprising a plurality of contractions of the individual's heart which includes contraction c to provide an averaged seismocardiogram waveform corresponding to contraction c, and identifying a first fiducial point indicating opening of the aortic valve for contraction c in the averaged seismocardiogram waveform, and
    (ii) recursively determine a pre-ejection period (PEP) for each contraction c of the individual's heart during time n by determining a time difference between a second fiducial point in the time-dependent electrocardiogram waveform indicating the onset of electrical stimulation of the ventricles during contraction c and the first fiducial point indicating opening of the aortic valve for contraction c.

2. A system according to claim 1, further comprising:
a plethysmogram sensor apparatus configured to be worn on the patient's body and detect signals indicative of changes in blood volume at an extremity produced due to contraction of the individual's heart for time n and generate therefrom a time-dependent plethysmogram waveform.

3. A system according to claim 2, wherein the plethysmogram sensor apparatus is configured to be worn at the base of the patient's thumb or finger.

4. A system according to claim 3, wherein the processing apparatus is operably connected to the third body-worn sensor and is configured to recursively determine a Pulse Arrival Time (PAT) for each contraction c of the individual's heart during time n by determining a time difference between the second fiducial point in the time-dependent electrocardiogram waveform indicating the onset of electrical stimulation of the ventricles during contraction c and a third fiducial point in the time-dependent plethysmogram waveform indicating arrival of the pressure wave at the extremity due to contraction c.

5. A system according to claim 1, wherein the processing apparatus is further configured to recursively determine an estimated time of aortic valve closure for each contraction c of the individual's heart during time n.

6. A system according to claim 1, wherein the processing apparatus is further configured to recursively determine an estimated time of mitral valve closure for each contraction c of the individual's heart during time n.

7. A system according to claim 1, wherein time n is at least one hour.

8. A system according to claim 1, wherein the length of the moving window is between 15 seconds and 2 minutes.

* * * * *